United States Patent [19]

Yamamoto et al.

[11] Patent Number: 4,923,119

[45] Date of Patent: May 8, 1990

[54] SUSTAINED-RELEASE PHEROMONE DISPENSER

[75] Inventors: Akira Yamamoto; Ryuichi Saguchi; Shigehiro Nagura, all of Niigata, Japan

[73] Assignee: Shin-Etsu Chemical Co., Ltd., Tokyo, Japan

[21] Appl. No.: 351,200

[22] Filed: May 12, 1989

[30] Foreign Application Priority Data

May 13, 1988 [JP] Japan .............................. 63-116650
Sep. 29, 1988 [JP] Japan .............................. 63-245417

[51] Int. Cl.$^5$ ............................................ A01N 25/02
[52] U.S. Cl. ........................................ 239/55; 424/84; 424/443; 424/473
[58] Field of Search ........................ 239/34, 53, 55, 56, 239/60; 424/84, 443, 473

[56] References Cited

U.S. PATENT DOCUMENTS

| | | | |
|---|---|---|---|
| 4,014,334 | 3/1977 | Theeuwes et al. | 424/473 X |
| 4,161,283 | 7/1979 | Hyman | 239/55 |
| 4,445,641 | 5/1984 | Baker et al. | 239/56 X |
| 4,605,165 | 8/1986 | Van Loveren et al. | 239/56 X |
| 4,666,767 | 5/1987 | Von Kohorn et al. | 424/83 X |
| 4,834,745 | 5/1989 | Ogawa et al. | 424/405 X |

Primary Examiner—Andres Kashnikow
Assistant Examiner—William Grant
Attorney, Agent, or Firm—Jules E. Goldberg

[57] ABSTRACT

A bag-like dispenser is proposed which contains a sex pheromone compound of insects and is used for sustainedly releasing the pheromone compound at a uniform emission rate over a long period of time so as to exhibit effectiveness for the population control of pests by distributing a number of the dispensers over fields. The bag-like dispenser body is formed of a specific polymeric laminate film having a thickness of 20–200 μm and composed of at least two layers or, preferably, of three layers, in which one of the layers is a film of a polymer or copolymer of vinylidene chloride having a thickness of 4–20 μm as the intermediate layer of the three-layered laminate and the other layer or each of the other layers is a film of a specific polymer having a specified thickness, such as a film of a polyolefin, copolymer of ethylene and vinyl acetate, poly(vinyl chloride), copolymer of vinyl chloride and vinyl acetate and the like.

5 Claims, 2 Drawing Sheets

SUSTAINED-RELEASE PHEROMONE DISPENSER

BACKGROUND OF THE INVENTION

The present invention relates to a sustained-release pheromone dispenser or, more particularly, to a pheromone dispenser capable of sustainedly emitting a sex pheromone compound used for population control of an insectan pest to the environment at a constant rate over a long period of time.

Many proposals have been made and are under practice in the prior art for sustainedly emitting a sex pheromone compound and the like effective for population control of a pest as contained in a suitable container to the environment at a constant rate of emission over a length of time. These prior art proposals can be classified into several types. The first type proposals are for a pheromone dispenser in which the sex pheromone compound is supported as being adsorbed by a suitable adsorbent as a carrier or as being admixed with a polymeric resin forming a carrier layer. For example, U.S. Pat. No. 4,017,030 discloses a pheromone dispenser in which the sex pheromone compound is contained in a capillary tube having an open end and emitted from the open end of the tube. Pheromone dispensers of this type have a defect in respect of the usually very short serviceable life because a single dispenser can contain only an extremely small amount of the pheromone compound. U.S. Pat. No. 4,160,335 discloses a pheromone dispenser having a multilayered laminate of polymeric films to serve as a carrier of the pheromone compound with an object of controlling the rate of pheromone emission from a pheromone-carrying layer of a polymeric resin admixed with the pheromone compound. Pheromone dispensers of this type have a serious disadvantage that, while the rate of pheromone emission is sometimes too large in the initial stage of exposure thereof to the open field, the rate gradually decreases in the lapse of time and, moreover, a considerable amount of the pheromone compound initially contained in the dispenser remains unreleased out of the dispenser to cause a large loss of the expensive compound.

Further, West German Patent No. 2,832,248 discloses a dispenser of (S)-cis-verbenol and methyl butenol as an attractant of wood borers, i.e. *Limonoria lignorum*, in which the attractant compounds are absorbed by a porous carrier and wrapped with a film of a plastic resin such as polyethylene and the like. West German Patent No. 2,945,655 discloses a dispenser of the same attractant in which the chemicals are mixed with a pasty base and a plastic bag is filled with the mixture. Japanese Patent Kokai 59-13701 and U.S. Pat. No. 4,445,641 describe a pheromone dispenser in which the pheromone compound is absorbed by a porous carrier and the pheromone-holding carrier is coated with a coating film of polyethylene and the like to control the emission rate of the pheromone compound through the coating film. These pheromone dispensers have a disadvantage in common that a considerable proportion of the pheromone compound absorbed in the carrier remains in the carrier unreleased even after prolonged exposure to the atmosphere to cause a large loss of the pheromone compound.

As is understood from the above discussion, important characteristics required for a pheromone dispenser are that the pheromone compound contained in the dispenser is emitted to the ambience at a constant rate over a long period of field exposure and that the pheromone compound initially contained in the dispenser is released out of the dispenser as completely as possible so as to minimize the loss of the expensive pheromone compound remaining as unutilized. These requirements can be satisfied by a dispenser in which a liquid pheromone compound is contained and sealed in a container having a wall provided with a barrier layer capable of exhibiting an adequate permeability to the liquid compound contained therein.

The prior art pheromone dispensers belonging to the second type of the proposals are further classified into three classes including so-called microcapsules containing the pheromone compound as the core material disclosed in U.S. Pat. No. 2,800,457, No. 2,800,458 and No. 3,577,515 and elsewhere, capillary tubes of polyethylene containing the liquid pheromone compound and sealed at the ends disclosed in Japanese Patent Kokai 56-142202, 57-9705, 57-45101, 57-72904, 57-156403, 59-216802 and 60-215367 and elsewhere, and those in which the pheromone compound is wrapped in a sheet or bag of a plastic film disclosed in Journal of Economic Entomology, volume 62, No. 2, pages 517–518 (1969).

The microcapsules of the above mentioned first class are not so widely utilized in practice because of the high costs for the preparation, large loss of the pheromone compound in the process of encapsulation into microcapsules and too large rate of pheromone emission and short serviceable life as a consequence of the extremely large surface area of the microcapsules. In respect of the capillary tube-type dispensers as the second class, various improvements have been attempted by using a polyethylene tube of adequate wall thickness or by combining the polyethylene tube with a metal wire side-by-side to facilitate the hanging works on the tree twigs. Though advantageous in respect of the sustained releasability and relatively long life for service, it is reported in Journal of Economic Entomology, volume 75, No. 6, pages 1431–1436 (1985) that these tubular dispensers have a defect that the rate of pheromone emission is subject to a considerable decrease in the latter half stage of the life on service. The journal article recited for the plastic sheet- or bag-wrapped pheromone dispenser describes an example in which (Z)-7-dodecenyl acetate, which is a sex pheromone of cabbage loopers, is enclosed and sealed together with sand in a bag of 3 cm by 5 cm wide made of a polyethylene film having a thickness of 50 to 150 $\mu$m and is used for the purpose of intercommunication disruption. Although uniformity is obtained in the rate of pheromone emission, pheromone dispensers of this type have a disadvantage of a short life of service for only about two weeks or so because polyethylene works only insufficiently as a barrier against permeation of the pheromone compound.

Dispensers of the third type in the prior art are proposed in U.S. Pat. No. 3,343,663, No. 3,785,556 and No. 4,161,283 and elsewhere in which a biologically active vaporizable substance other than sex pheromones of insects and the like, is wrapped with a sheet or a bag made of a plastic film and the compound is emitted to the atmosphere at a controlled rate through the plastic film.

Although a variety of different types of pheromone dispensers have been proposed as is described above, those by using a capillary tube made of polyethylene and by using a plastic film or bag are the only examples of the pheromone dispensers used for the purpose of intercommunication disruption or population control of pests each containing at least 40 mg of a sex pheromone compound which is an unsaturated aliphatic ester, aldehyde or ketone having 12 to 20 carbon atoms in a molecule. These dispensers are all made by using polyethylene as a material of the dispenser body. This is because this polymeric material has an adequate affinity with pheromone compounds but is inert thereto absorbing only a very small amount thereof, has excellent workability such as good weldability in the sealing works of the dispenser body containing the pheromone compound and has excellent mechanical strengths and resistance against water as the essential properties required for pheromone dispensers.

The tubular dispensers have a defect that, although the rate of pheromone emission can be controlled over two months or longer as a consequence of the wall thickness of at least 300 $\mu$m of the capillary tube of polyethylene, the rate of pheromone emission is subject to a considerable decrease in the latter half of the life for service. The bag-like dispensers are under a limitation in respect of the workability of a plastic film into bags that the plastic film must have a thickness not exceeding 200 $\mu$m so that bag-type dispensers made from polyethylene alone have a limited life of service and are not suitable for the purpose of emission control over two months or longer as in the tubular dispensers because polyethylene cannot provide a sufficient barrier. When the temperature of ambience is high and the wind velocity is low, in addition, the vaporization velocity of the pheromone compound from the dispenser walls would be too low to dissipate the whole amount of the pheromone compound having reached the outer surface of the dispenser after permeation through the polyethylene walls so that the outer surface the dispenser is always wettish with the pheromone compound oozing out to increase deposition of dusts with great troubles in the outdoor use of the dispensers.

As is described above, there is known no high-performance pheromone dispenser in which a plastic film having a thickness of 200 $\mu$m or smaller serves as a barrier against permeation of the pheromone compound enabling control of the rate of pheromone emission over a period of at least two months without a wettish condition of the surface. The inventors have continued extensive investigations to develop a sustained-release dispenser of a sex pheromone compound of insects which is an aliphatic unsaturated acetate, aldehyde or ketone compound, of which the amount of the pheromone compound contained in a single dispenser is at least 40 mg, and arrived at a conclusion that a sustained-release pheromone dispenser could well satisfy the requirements without the problems and disadvantages in the tubular or bag-like dispensers in the prior art.

SUMMARY OF THE INVENTION

Thus, the sustained-release pheromone dispenser of the present invention comprises:

(A) a pheromone compound; and (B) a bag containing the pheromone compound made at least partly of a laminate film of an overall thickness in the range from 20 to 200 $\mu$m composed of at least two layers, of which one is a film of a poly(vinylidene chloride) or a copolymer mainly composed of vinylidene chloride having a thickness in the range from 4 to 20 $\mu$m and the other or each of the others, the thickness or overall thickness being in the range from 10 to 196 $\mu$m, is a film of a polymer selected from the group consisting of polyolefins, copolymers of ethylene and vinyl acetate, polymers of vinyl chloride and copolymers thereof, polymers of an acrylic acid ester or copolymers thereof, polymers of a methacrylic acid ester and copolymers thereof, cellulose esters and cellulose ethers.

In particular, the above mentioned laminate film is composed of three layers of which the intermediate layer is made of a film of a polymer or copolymer of vinylidene chloride having a thickness in the range from 4 to 20 $\mu$m, the outer layer is a film of a polyolefin or a copolymer of ethylene and vinyl acetate having a thickness in the range from 10 to 100 $\mu$m and the inner layer is a film of a polymer selected from the group consisting of polyolefins, copolymers of ethylene and vinyl acetate, poly(vinyl chloride) and copolymers of vinyl chloride and vinyl acetate having a thickness in the range from 5 to 100 $\mu$m.

DETAILED DESCRIPTION OF THE PREFERRED EMBODIMENTS

As is described above, the body of the inventive pheromone dispenser is a bag made of a plastic film and at least a part of the bag walls is made of a laminate film composed of at least two different plastic films of a specific polymeric resin. In the following, the cross sectional structure of the bag body is described in detail with reference to the accompanying drawing.

Figure 1:
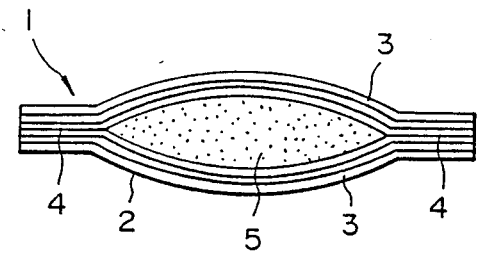
FIG. 1 is a cross sectional view of the inventive sustained-release pheromone dispenser.
Figure 3:
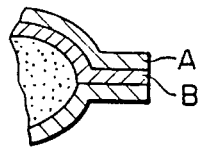
FIGS. 3 to 9 are each an enlarged partial cross sectional view of one of different embodiments of the inventive pheromone dispensers.
Figure 4:
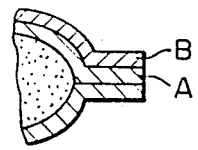
Figure 6:
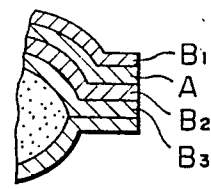
Figure 7:
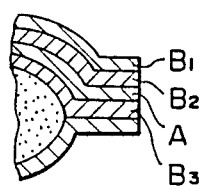
Figure 8:
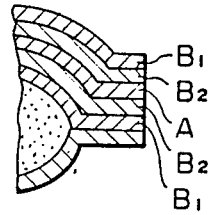

FIG. 1 illustrates a cross sectional view of the inventive sustained-release pheromone dispenser 1, the body of which is a bag 2 formed of a laminated film 3 by adhesively bonding or welding two sheets of the same along the periphery 4 to contain a liquid pheromone compound 5 enclosed therein. The laminate film 3 is composed of at least two layers of which one is a film A of a poly(vinylidene chloride) or a copolymer mainly composed of vinylidene chloride and the other or each of the others B is a film of a polymer different from polymers of vinylidene chloride. As is illustrated in FIGS. 3 and 4, the film A forms the outer layer or inner layer, respectively, with the film B forming the inner layer or the outer layer. When the layer B is formed of several films $B_1$, $B_2$, ... of different polymers, the laminating order of these films and the film A is also not limitative including the orders of, for example, $B_1$-A-$B_2$ in a three-ply laminate shown in FIG. 5, $B_1$-A-$B_2$-$B_3$ in a four-ply laminate shown in FIG. 6, $B_1$-$B_2$-A-$B_3$ in a four-ply laminate shown in FIG. 7, $B_1$-$B_2$-A-$B_2$-$B_1$ in a five-ply laminate shown in FIG. 8 and so on to be selected according to need.

In the pheromone dispenser of the invention, one of the layers in these multi-ply laminates is a film of a poly(vinylidene chloride) or a copolymer mainly composed of vinylidene chloride having a thickness in the range from 4 to 20 $\mu$m. The use of a film A of the specific polymeric resin can overcome the problems and disadvantages in the conventional bag-like pheromone dispensers that the barrier action against permeation of the pheromone compound through the bag walls is low and effective control of the emission rate of the pheromone can be obtained only for a very limited period of time and that, when the pheromone dispenser is exposed to an ambience at a relatively high temperature under weak wind blow, the permeation rate of the pheromone compound through the polymeric bag wall is so high as to exceed the vaporization rate of the pheromone compound from the bag surface so that the surface of the bag is wettish with the liquid pheromone compound to accelerate deposition of dusts on the surface resulting in an undesirable decrease in the performance of the pheromone dispenser.

When the thickness of the layer A exceeds 20 $\mu$m, the barrier action by the layer is too strong so that the rate of pheromone emission may be too low. When the thickness of the layer A is smaller than 4 $\mu$m, on the other hand, the layer serves as a barrier only insufficiently. The copolymer of vinylidene chloride here implied is a copolymer of which at least 50% by weight is the moiety of vinylidene chloride, the rest being the moiety of other monomers such as vinyl chloride, acrylic acid, acrylic acid esters, vinyl acetate, acrylonitrile and the like.

The other layer or layers than the layer A is a film or are films made from a polymer selected from the group consisting of polyolefins, e.g., polyethylene and polypropylene, copolymers of ethylene and vinyl acetate, poly(vinyl chloride) and copolymers of vinyl chloride, polymers and copolymers of acrylic acid esters, polymers and copolymers of methacrylic acid esters, cellulose esters and cellulose ethers such as ethyl cellulose. The barrier action of these layers is lower than the layer A made from a poly(vinylidene chloride) or a copolymer of vinylidene chloride to permit permeation of the pheromone compound therethrough. These layers B serve to reinforce the layer A having a thickness of 4 to 20 $\mu$m which alone has low mechanical strengths not to ensure practical use of the bag-like dispensers made of such a film alone. In addition, the above mentioned polymers have a relatively high affinity with the pheromone compound so that the layer or layers B exhibit a buffer action to impart the dispenser with adaptability to the changes in the outer environmental conditions such as temperature and wind velocity so that the problem of wettish bag surface with the pheromone compound due to adverse changes in the meteorological elements can be solved more completely. When the layer B is used as the inner layer of the bag, moreover, the heat-sealability of the laminate films can be greatly improved. In this regard, in particular, it is advantageous that the layer A is sandwiched with the layers of B forming the outermost and innermost layers. When two or more of the layers B are provided, the overall thickness of the layers B should be in the range from 10 to 196 $\mu$m.

Figure 5:
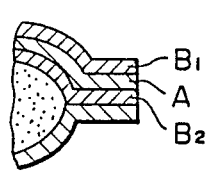

FIG. 5 illustrates a particular example of such a laminate film by a cross section, which is composed of the outermost layer $B_1$ of a polyolefin, e.g., polyethylene or polypropylene, or a copolymer of ethylene and vinyl acetate having a thickness of 10 to 100 $\mu$m, the intermediate layer A of a polymer or copolymer of vinylidene chloride having a thickness of 4 to 20 $\mu$m and the innermost layer $B_2$ of a polymeric resin with good heat-sealability and relatively high permeability to the pheromone compound such as a polyolefin, e.g., polyethylene and polypropylene, copolymer of ethylene and vinyl acetate, poly(vinyl chloride), copolymer of vinyl chloride and vinyl acetate and the like having a thickness of 5 to 100 $\mu$m. When the outermost layer $B_1$ has a thickness smaller than 10 $\mu$m, the performance of the laminate film is undesirably decreased. When the outermost layer has a thickness larger than 100 $\mu$m, on the other hand, the workability of the laminate film into bags is undesirably decreased. The innermost layer $B_2$ not only plays a role to impart heat-sealability to the laminate film but also contributes to reinforce and stabilize the intermediate layer. These effects of the innermost layer would be decreased when the thickness thereof is smaller than 5 $\mu$m while the workability of the laminate film into bags would be decreased when the thickness of the layer is larger than 100 $\mu$m.

The overall thickness of the laminate film is essentially in the range from 20 to 200 $\mu$m. When the thickness exceeds 200 $\mu$m, the uniformity of the emission rate of the pheromone compound, which is the largest advantage of the bag-like pheromone dispensers, cannot be ensured in addition to the decrease in the workability of the laminate film into bags. When the thickness of the laminate film is smaller than 20 $\mu$m, on the other hand, the laminate film is poor in the mechanical strengths so that the dispenser body made therefrom cannot withstand handling in the practical use.

It is optional according to need that each of the above mentioned polymeric resins forming the layers A and B is admixed with various kinds of additives such as ultraviolet absorbers, plasticizers, stabilizers, stabilizing aids, processing aids, lubricants and others.

The pheromone compound contained in the bag-like pheromone dispenser is released to the environment by permeating the laminate film. Needless to say, the rate of pheromone emission depends on the surface area of the bag-like dispenser body increasing as the surface area increases. In this regard, it is important that the effective surface area of the bag made of the laminate film and available for the emission of the pheromone compound is in the range from 100 to 6000 $mm^2$ excepting the sealed portions by appropriately designing the dispenser body.

Figure 9:
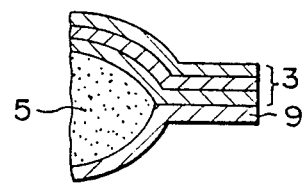

The laminate film can be fabricated into a bag-like dispenser body in a variety of ways. For example, two rectangular sheets of the laminate film having the same size are laid one on the other and the two sheets are bonded by welding along the four sides of the rectangular form to give a four way-sealed bag. Alternatively, a single rectangular sheet of the laminate film is folded along the center line and the two flaps of the thus folded sheet are bonded together by heat-sealing along the three free sides to give a three way-sealed bag. Pillow-wrapping bags and stick-wrapping bags can also be used. As is illustrated in FIG. 9, the dispenser body can be a four way-sealed bag made of two different polymeric sheets of which one is a layer 3 of the laminate film and the other is a layer 9 of a film of a polymer having no permeability to the pheromone compound. Such a four way-sealed bag is advantageous in respect of the relatively large capacity of the pheromone compound contained in the bag per unit area of the effective surface so that portionwise enclosing work of the pheromone compound is facilitated, especially, when it is required that each pheromone dispenser has a limited effective surface area.

The above mentioned pheromone-impermeable sheet can be made from various kinds of materials such as a foil of a metal, e.g., aluminum, cellophane, films of polyvinyl alcohol, films of nylon or a poly(ethylene terephthalate) having a thickness of 20 $\mu$m or larger and the like. If necessary, these pheromone-impermeable sheets can be laminated with a film of a polymer having heat-sealability such as polyethylene, copolymers of ethylene and vinyl acetate and the like. Such a laminate film can be prepared by a conventional method including bonding by using an adhesive, co-extrusion molding and so on.

The liquid pheromone compound 5 to be enclosed in the bag 2 is mostly a compound selected from the group of aliphatically unsaturated hydrocarbons, acetates, aldehydes and ketones having 12 to 20 carbon atoms in a molecule known as a sex pheromone compound of a pest belonging to the genera of lepidopteran insects. Examples of such a pheromone compound include hydrocarbon compounds such as (Z)-9-tricosene, 14-methyl-1-octadecene and the like, acetate compounds such as (E)-5-decenyl acetate, (E)-4-tridecenyl acetate, (Z)-7-dodecenyl acetate, (Z)-8-dodecenyl acetate, (Z)-9-dodecenyl acetate, (E)-9-dodecenyl acetate, 11-dodecenyl acetate, (E,Z)-7,9-dodecadienyl acetate, (Z)-7-tetradecenyl acetate, (Z)-9-tetradecenyl acetate, (Z)-11-tetradecenyl acetate, (Z)-11-hexadecenyl acetate, (E,Z)-3,13-octadecadienyl acetate, (E,Z)-2,13-octadecadienyl acetate, (Z,Z)-3,13-octadecadienyl acetate, (Z,E)-9,11-tetradecadienyl acetate, (Z,E)-9,12-tetradecadienyl acetate, (Z,Z/E)-7,11-hexadecadienyl acetate and the like, aldehyde compounds such as (Z)-7-tetradecenal, (Z)-9-tetradecen-al, (Z)-11-tetradecenal,(Z)-7-hexadecenal, (Z)-9-hexadecenal,(Z)-11-hexadecenal,n-hexadecanal,(Z,Z)-11,13-hexadecadienal,(Z)-13-octadecenal and the like and ketone compounds such as (Z)-13-icosen-10-one and the like as well as mixtures thereof and mixtures mainly composed thereof with other compounds. These phe-romone compounds can optionally be admixed with additives such as antioxidants, ultraviolet absorbers and the like.

The pheromone dispensers of the invention can be manufactured by using known machines for the respective steps including the bag making step from the laminate film 3 into bags 2, filling of the bags 2 with the liquid pheromone compound 5, sealing of the bags 2, and cutting and trimming of the individual bags 2. Sealing of the laminate films is performed preferably by the heat-sealing method, impulse-sealing method or ultrasonic-sealing method. It is optional that the surface of the bag-like dispenser is covered with a film impermeable to the pheromone compound which is removed just before the dispenser is brought to use in the field.

Following is a description of one of the preferable embodiments of the inventive bag-like pheromone dispenser. Thus, the laminate film is composed of three layers including the intermediate layer made of a film of a polymer or copolymer of vinylidene chloride having a thickness in the range from 4 ro 20 μm, the outer layer made of a film of a polyolefin or a copolymer of ethylene and vinyl acetate having a thickness in the range from 10 to 100 μm and the inner layer made of a film of a polymer selected from the group consisting of polyolefins, copolymers of ethylene and vinyl acetate, poly(vinyl chloride) and copolymers of vinyl chloride and vinyl acetate having a thickness in the range from 5 to 100 μm and the overall thickness of the laminate film is in the range from 20 to 200 μm. The dispenser body should preferably have an effective area made of the above defined laminate film and available for the emission of the pheromone compound in the range from 100 to 6000 mm².

Figure 2:
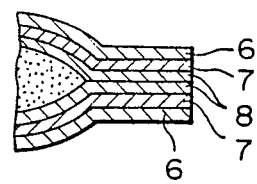
FIG. 2 is an enlarged partial cross sectional view of the dispenser illustrated in FIG. 1.

FIG. 2 illustrates a partial cross sectional view of a bag-like pheromone dispenser made of the above defined three-layered laminate film composed of the outer layer 6, intermediate layer 7 and inner layer 8. The intermediate layer is made of a polymer or copolymer of vinylidene chloride. The copolymer of vinylidene chloride here implied is a copolymer composed of at least 50% by weight of the vinylidene chloride moiety and the balance is a moiety of vinyl chloride, acrylic acid, esters of acrylic acid, vinyl acetate, acrylonitrile and the like. This intermediate layer serves as a barrier against permeation of the pheromone compound contained in the dispenser and, in this regard, the thickness thereof is necessarily in the range from 4 to 20 μm.

The outer layer of the laminate film forming the inventive pheromone dispenser is made of a film of a polyolefin, e.g., polyethylene and polypropylene, or a copolymer of ethylene and vinyl acetate having a thickness of 10 to 100 μm. As a consequence of the use of such an outer layer, the problem of a wettish surface in the prior art dispensers as a result of changes in the meteorological conditions can be solved. This is presumably because the polymer has high affinity with the pheromone compound to comply with the changes in the ambient conditions such as temperature and wind velocity to exhibit a buffer action although the layer made from such a polymer serves less as a barrier for the permeation of the pheromone compound than the intermediate layer. Such advantageous performance cannot be fully exhibited when the outer layer has a thickness smaller than 10 μm while the laminate film is poor in the workability into bags when the outer layer has a thickness larger than 100 μm.

The inner layer made from the above specified polymer serves to impart the laminate film with heat-sealability and also to reinforce and stabilize the intermediate layer. Such effects cannot be fully exhibited when the inner layer has a thickness smaller than 5 μm while the laminate film is poor in the workability into bags when the inner layer has a thickness larger than 100 μm.

In the following, the sustained-release pheromone dispenser of the present invention is described in more detail by way of examples and comparative examples.

EXAMPLE 1

A three-layered laminate film having an overall thickness of 63 μm was prepared by sandwiching a film of a poly(vinylidene chloride) having a thickness of 9 μm as the intermediate layer with two films of a low-density polyethylene each having a thickness of 27 μm. Two rectangular sheets of this laminate film were stacked one on the other and heat-sealed together along the four sides of a 20 mm by 30 mm rectangle in the inside measure to form a bag which had an effective surface area of 1200 mm². This bag was filled with 80 mg of (Z,Z/E)-7,11-hexadecadienyl acetate known as the sex pheromone compound of pinkball worms.

This sustained-release pheromone dispenser was kept standing at a temperature of 30° C. in a wind blowing at a velocity of 0.5 meter/second and the rate of pheromone emission therefrom was monitored over a period of 120 days or longer to find that the rate of pheromone emission was quite uniform over the testing period at 0.5 mg/day. No wettishness was found on the surface of the bag which might possibly be caused by the overly permeation of the liquid pheromone compound through the laminate film.

COMPARATIVE EXAMPLE 1

The experimental procedure was the same as in Example 1 excepting replacement of the three-layered laminate film with a single-layered low-density polyethylene film having a thickness of 60 μm. The results were that the surface of the bag-like dispenser body was wettish with the liquid pheromone compound due to the excessively large permeation velocity of the pheromone compound through the film so that satisfactory performance could not be expected for the pheromone dispenser.

COMPARATIVE EXAMPLE 2

The experimental procedure was substantially the same as in Example 1 excepting replacement of the three-layered laminate film with a single-layered film of a poly(vinylidene chloride) resin having a thickness of 9 μm. The results were that the rate of pheromone emission was uniform at 0.5 mg/day over the testing period and the surface of the dispenser bag was little wettish. A problem, however, was that the bag had low mechanical strengths and was liable to be broken unless it was handled with great care so that the practical value of such a pheromone dispenser was found low.

COMPARATIVE EXAMPLE 3

The experimental procedure was substantially the same as in Example 1 excepting replacement of the three-layered laminate film fith another three-layered laminate film having an overall thickness of 90 μm and prepared by sandwiching a film of a poly(vinylidene chloride) resin having a thickness of 30 μm with two low-density polyethylene films each having a thickness of 30 μm. The results were that the rate of pheromone emission therefrom was extremely low with a low practical value as a pheromone dispenser.

EXAMPLE 2

The experimental procedure was substantially the same as in Example 1 excepting replacement of the three-layered laminate film with another three-layered laminate film having an overall thickness of 24 μm and prepared by sandwiching a film of a poly(vinylidene chloride) resin having a thickness of 4 μm as the intermediate layer with a polypropylene film having a thickness of 10 μm as the outer layer and a film of a copolymer of ethylene and vinyl acetate having a thickness of 10 μm as the inner layer. The results were that a uniform emission rate of 0.7 mg/day of the pheromone compound could be maintained for 100 days or longer and no wettishness of the bag surface was noted indicating usefulness of the pheromone dispenser in practical applications.

EXAMPLE 3

The experimental procedure was substantially the same as in Example 1 excepting replacement of the three-layered laminate film with a two-layered laminate film having an overall thickness of 35 μm and composed of a film of a poly(vinylidene chloride) having a thickness of 5 μm as the outer layer and a film of a copolymer of 88% by weight of ethylene and 12% by weight of vinyl acetate having a thickness of 30 μm as the inner layer. The results were that a uniform emission rate of 0.7 mg/day of the pheromone compound could be maintained for 100 days or longer and no wettishness of the bag surface as noted indicating usefulness of the pheromone dispenser in practical applications.

EXAMPLE 4 TO 13

Nine different types of bag-like pheromone dispensers were prepared by using different laminate films indicated in Table 1 below and enclosing each 80 mg of different pheromone compounds also indicated in Table 1. These pheromone dispensers were tested under the same conditions as in Example 1. A uniform emission rate of the pheromone compound shown in Table 1 could be obtained in each type of the dispensers over a period of at least 60 days. Wettishness of the surface was noted in none of the dispensers and each of the dispensers had a mechanical strength to withstand handling without particular carefulness.

The constitution of each laminate film is shown in the table by the kinds of the polymeric resins $A_1$ and $A_2$ and $B_1$ to $B_6$ shown below and the thickness in μm of each layer in brackets in an order from the outermost layer to the innermost layer. The bags in Examples 6 and 10 were prepared by using the pheromone-permeable laminate film for one side alone and the other side of the bag was formed of a pheromone-impermeable film which was a laminate film of a poly(ethylene terephthalate) film and a low-density polyethylene film in Example 6 and a laminate film of an aluminum foil and a low-density polyethylene film in Example 10. The amount of the enclosed pheromone compound was increased to 160 mg in Example 13.

Polymeric resin of laminate layers
$A_1$: poly(vinylidene chloride)
$A_2$: 8:2 by weight copolymer of vinylidene chloride and vinyl chloride
$B_1$: low-density polyethylene
$B_2$: high-density polyethylene
$B_3$: polypropylene
$B_4$: poly(vinyl chloride)
$B_5$: poly(methyl acrylate)
$B_6$: cellulose acetate The pheromone compound enclosed in each of the pheromone dispensers was as shown below.
HDDA: (Z,Z/E)-7,11-hexadecadienylacetate
TDA: (Z)-11-tetradecenylacetate
ICN: (Z)-icosen-11-one
HDAL: (Z)-11-hexadecenal
DDA: (Z)-8-dodecenylacetate

TABLE 1

| Example No. | Laminate film Polymer of layer (thickness, μm) (outermost - innermost) | Overall thickness, μm | Bag Effective surface area, mm² | Dimensions (inside measure) | Pheromone compound | Emission rate, mg/day |
| --- | --- | --- | --- | --- | --- | --- |
| 4 | $B_1$(27) - $A_1$(9) - $B_1$(27) | 63 | 1200 | 20 mm × 30 mm | HDAL | 0.6 |
| 5 | $B_1$(27) - $A_1$(9) - $B_1$(27) | 63 | 1200 | 20 mm × 30 mm | ICN | 0.2 |
| 6 | $B_2$(15) - $A_1$(8) - $B_1$(20) | 43 | 600* | 20 mm × 30 mm | TDA | 0.6 |

TABLE 1-continued

| Example No. | Laminate film Polymer of layer (thickness, μm) (outermost - innermost) | Overall thickness, μm | Bag Effective surface area, mm² | Dimensions (inside measure) | Pheromone compound | Emission rate, mg/day |
| --- | --- | --- | --- | --- | --- | --- |
| 7 | B₁(45) - A₂(12) - B₁(45) | 102 | 1800 | 30 mm × 30 mm | HDDA | 0.6 |
| 8 | B₁(100) - A₁(18) - B₁(62) | 180 | 1200 | 20 mm × 30 mm | DDA | 0.8 |
| 9 | B₃(10) - A₂(4) - B₁(10) | 24 | 1200 | 20 mm × 30 mm | HDDA | 0.7 |
| 10 | B₂(20) - A₂(8) - B₁(15) | 43 | 600* | 20 mm × 30 mm | TDA | 0.6 |
| 11 | B₁(20) - B₄(22) - A₂(18) - B₁(100) | 160 | 1800 | 30 mm × 30 mm | DDA | 0.8 |
| 12 | B₁(10) - B₅(10) - A₂(9) - B₆(10) - B₁(10) | 49 | 1800 | 30 mm × 30 mm | HDDA | 0.7 |
| 13 | B₁(45) - A₂(12) - B₁(45) | 102 | 5600 | 70 mm × 40 mm | HDDA | 1.9 |

*pheromone-impermeable film for one side, see text.

What is claimed is:

1. A sustained-release dispenser of a sex pheromone compound of insects which comprises:
   (a) a sex pheromone compound of insects in the form of liquid; and
   (b) a bag containing the sex pheromone compound made at least partly of a laminate film having a thickness in the range from 20 μm to 200 μm and composed of at least two layers, of which (A) one is a film of a poly(vinylidene chloride) or a copolymer mainly composed of vinylidene chloride having a thickness in the range from 4 μm to 20 μm and (B) the other or each of the others, the thickness or total thick-ness thereof being in the range from 10 μm to 196 μm, is a film of a polymer selected from the group consisting of polyolefins, copolymers of ethylene and vinyl acetate, polymers and copolymers of vinyl chloride, polymers and copolymers of an acrylic acid ester, cellulose esters and cellulose ethers.

2. The sustained-release dispenser of a sex pheromone compound of insects as claimed in claim 1 wherein the laminate film is composed of three layers of which the outer layer facing outside of the bag is a film of a polyolefin or a copolymer of ethylene and vinyl acetate having a thickness in the range from 10 μm to 100 μm, the intermediate layer is a film of a polymer or copolymer of vinylidene chloride having a thickness in the range from 4 μm to 20 μm and the inner layer facing inside of the bag is a film of a polymer selected from the group consisting of polyolefins, copolymers of ethylene and vinyl acetate, poly(vinyl chloride) and copolymers of vinyl chloride and vinyl acetate having a thickness in the range from 5 μm to 100 μm.

3. The sustained-release dispenser of a sex pheromone compound of insects as claimed in claim 1 wherein a portion of the bag having an area in the range from 100 mm² to 6000 mm² is made of the laminate film.

4. The sustained-release dispenser of a sex pheromone compound of insects as claimed in claim 1 wherein the copolymer mainly composed of vinylidene chloride contains at least 50% by weight of the vinylidene chloride moiety, the balance being the moiety of a monomer or monomers selected from the group consisting of vinyl chloride, acrylic acid, acrylic acid esters, vinyl chloride and acrylonitrile.

5. A sustained-release dispenser of a sex pheromone compound of insects, which is a compound selected from the group consisting of aliphatically unsaturated hydrocarbon compounds, acetates, aldehydes and ketons having 12 to 20 carbon atoms in a molecule in the form of liquid, which comprises:
   (a) the sex pheromone compound of insects; and
   (b) a bag containing the sex pheromone compound made at least partly of a laminate film having a thickness in the range from 20 μm to 200 μm and composed of at least two layers, of which (A) one is a film of a poly(vinylidene chloride) or a copolymer mainly composed of vinylidene chloride having a thickness in the range from 4 μm to 20 μm and (B) the other or each of the others, the thickness or total thickness thereof being in the range from 10 μm to 196 μm, is a film of a polymer selected from the group consisting of polyolefins, copolymers of ethylene and vinyl acetate, polymers and copolymers of vinyl chloride, polymers and copolymers of an acrylic acid ester, cellulose esters and cellulose ethers.

* * * * *